(12) United States Patent
Jakob et al.

(10) Patent No.: US 10,278,749 B2
(45) Date of Patent: May 7, 2019

(54) BONE PLATE FOR THE GREATER TROCHANTER

(71) Applicant: UNIVERSITATSSPITAL BASEL, Basel (CH)

(72) Inventors: Marcel Jakob, Basel (CH); Patrick Studer, Binningen (CH)

(73) Assignee: UNIVERSITATSSPITAL BASEL, Basel (CH)

( * ) Notice: Subject to any disclaimer, the term of this patent is extended or adjusted under 35 U.S.C. 154(b) by 895 days.

(21) Appl. No.: 14/405,413

(22) PCT Filed: Jun. 6, 2013

(86) PCT No.: PCT/EP2013/061746
§ 371 (c)(1),
(2) Date: Dec. 4, 2014

(87) PCT Pub. No.: WO2013/182656
PCT Pub. Date: Dec. 12, 2013

(65) Prior Publication Data
US 2015/0182266 A1 Jul. 2, 2015

(30) Foreign Application Priority Data

Jun. 6, 2012 (EP) .................................... 12171093

(51) Int. Cl.
*A61F 2/30* (2006.01)
*A61F 2/36* (2006.01)
*A61B 17/74* (2006.01)

(52) U.S. Cl.
CPC ............ *A61B 17/746* (2013.01); *A61B 17/74* (2013.01); *A61F 2/30739* (2013.01);
(Continued)

(58) Field of Classification Search
CPC ....... A61F 2/30739; A61F 2002/30192; A61B 17/74; A61B 17/746; A61B 17/744; A61B 17/8061; A61B 17/8085
See application file for complete search history.

(56) References Cited

U.S. PATENT DOCUMENTS 3,939,498 A * 2/1976 Lee ..................... A61F 2/30739
623/23.27
4,187,559 A * 2/1980 Grell .................... A61B 17/175
623/20.11
(Continued)

FOREIGN PATENT DOCUMENTS

| DE | 9003062 | 5/1990 |
|---|---|---|
| EP | 1464294 | 10/2004 |
| WO | WO2004/030550 | 4/2004 |

OTHER PUBLICATIONS

Kannus P, Parkkari J, Niemi S, et al. Prevention of hip fracture in elderly people with use of a hip protector. N Engl J Med 2000;343:1506-13.

(Continued)

*Primary Examiner* — David W Bates
(74) *Attorney, Agent, or Firm* — JMB Davis Ben-David (57) ABSTRACT

The invention relates to Implant device (1) comprising a rigid element (10) being designed to be fastened to a femur implant (20) in a fastened state of said rigid element (10), wherein particularly said femur implant (20) is an intramedullary nail or a femoral stem. According to the invention said rigid element (10) is designed as a hook-shaped plate (10) for encompassing the greater trochanter (3) of the femur (2) at least in sections when being arranged in said fastened state and when said femur implant (20) is arranged in or on the femur (2) as intended.

19 Claims, 7 Drawing Sheets

(52) U.S. Cl.
CPC .............. *A61B 17/744* (2013.01); *A61F 2/36* (2013.01); *A61F 2002/3054* (2013.01); *A61F 2002/30192* (2013.01)

(56) References Cited

U.S. PATENT DOCUMENTS

| | | | | |
|---|---|---|---|---|
| 4,978,349 | A * | 12/1990 | Frigg | A61B 17/1721 606/62 |
| 5,197,989 | A * | 3/1993 | Hinckfuss | A61F 2/30724 623/22.42 |
| 5,356,410 | A | 10/1994 | Pennig | |
| 5,376,126 | A * | 12/1994 | Lin | A61B 17/746 606/60 |
| 5,443,516 | A * | 8/1995 | Albrektsson | A61F 2/384 606/70 |
| 5,462,547 | A * | 10/1995 | Weigum | A61B 17/746 606/65 |
| 6,077,264 | A * | 6/2000 | Chemello | A61B 17/7225 606/62 |
| 6,379,390 | B1 | 4/2002 | Advani | A61F 2/3601 623/23.11 |
| 6,503,281 | B1 * | 1/2003 | Mallory | A61B 17/8061 623/22.11 |
| 7,179,259 | B1 * | 2/2007 | Gibbs | A61B 17/1753 606/64 |
| 7,931,691 | B2 * | 4/2011 | Li | A61B 17/86 623/22.4 |
| 8,252,061 | B2 * | 8/2012 | Mikami | A61F 2/30739 606/287 |
| 8,579,984 | B2 * | 11/2013 | Borowsky | A61B 17/74 623/19.14 |
| 8,979,940 | B2 * | 3/2015 | Porter | A61F 2/30739 623/23.15 |
| 9,050,150 | B2 * | 6/2015 | Vargas | A61B 17/74 |
| 9,254,154 | B2 * | 2/2016 | Gonzalez-Hernandez | A61B 17/8061 |
| 9,339,313 | B1 | 5/2016 | Powlan | A61B 17/746 |
| 9,402,667 | B2 * | 8/2016 | Gonzalez-Hernandez | A61B 17/8061 |
| 9,463,054 | B2 * | 10/2016 | Mueckter | A61B 17/72 |
| 9,675,400 | B2 * | 6/2017 | Katrana | A61B 17/8866 |
| 9,730,743 | B2 * | 8/2017 | Vargas | A61B 17/808 |
| 2004/0210220 | A1 * | 10/2004 | Tornier | A61B 17/8061 606/284 |
| 2004/0236337 | A1 * | 11/2004 | Deloge | A61B 17/74 606/74 |
| 2006/0142763 | A1 * | 6/2006 | Munro | A61B 17/744 606/62 |
| 2007/0185493 | A1 * | 8/2007 | Feibel | A61B 17/8061 606/71 |
| 2007/0225714 | A1 * | 9/2007 | Gradl | A61B 17/746 606/326 |
| 2008/0177393 | A1 * | 7/2008 | Grant | A61F 2/30734 623/18.11 |
| 2009/0069851 | A1 * | 3/2009 | Gillard | A61B 17/1684 606/280 |
| 2009/0164026 | A1 * | 6/2009 | Mikami | A61F 2/30739 623/23.15 |
| 2009/0312758 | A1 * | 12/2009 | Petit | A61B 17/74 606/60 |
| 2010/0234896 | A1 * | 9/2010 | Lorenz | A61B 17/74 606/286 |
| 2011/0112534 | A1 * | 5/2011 | Appenzeller | A61B 17/7233 606/62 |
| 2011/0160730 | A1 * | 6/2011 | Schonhardt | A61B 17/8061 606/71 |
| 2011/0218641 | A1 * | 9/2011 | Smith | A61F 2/32 623/22.42 |
| 2013/0116734 | A1 * | 5/2013 | Gonzalez-Hernandez | A61B 17/8061 606/286 |
| 2014/0052192 | A1 * | 2/2014 | Vargas | A61B 17/74 606/281 |
| 2015/0105779 | A1 * | 4/2015 | Smith | A61B 17/1725 606/71 |

OTHER PUBLICATIONS

Kannus P, Niemi S. Parkkari J, et al. Hip fractures in Finland between 1970 and 1997 and predictions for the future. Lancet 1999;353:802-5.

Gjertsen JE, Engesaeter LB, Fumes O, et al. The Norwegian hip fracture Register: Experiences after the first 2 years and 15'576 reported operations. Acta Orthop 2008;79(5):583-93.

Lohmann R, Frerichmann U, Stöckle U, et al. Proximal femoral fractures in the elderly. Analysis of data from health insurance providers on more than 23millions injured persons—part 1. Unfallchirurg. 2007;110(7):603-9.

Parker MJ, Handoll HH, Bhonsle S, et al. Condylocephalic nails versus extramedullary implants for extracapsular hip fractures. Cochrane Database Syst Rev. 2000;(2); CD 000338.

* cited by examiner

BONE PLATE FOR THE GREATER TROCHANTER

CROSS-REFERENCE TO RELATED APPLICATIONS

This is the U.S. National Stage of International Application No. PCT/EP2013/061746, filed Jun. 6, 2013, which was published in English under PCT Article 21(2), which in turn claims the benefit of EP Patent Application No. 12171093.3, filed Jun. 6, 2012.

The invention relates to an implant device according to the preamble of claim 1.

Such an implant device comprises a rigid element being designed to be fastened to a femur implant in a fastened state of said rigid element, wherein particularly said femur implant is an intramedullary nail or a femoral stem. Such a device relating to a femoral stem is described in US2009164026A1.

Hip fractures are among the most common types of fractures and a major cause of disability, functional impairment, and death in elderly people [1]. Due to demographic changes the number of fractures increased significantly during the last decades [2]. The incidence of an extracapsular proximal femoral fracture (OTA 31-A) lies around 90/100,000 inhabitants every year [3]. The "Bundesstelle für Qualitätssicherung (BQS)" in Germany reports 98,971 hip fractures in the year 2008 [4].

For the treatment of pertrochanteric fractures numerous implants are available. However, it is suggested that intramedullary (IM) nail fixation may be advantageous compared with extramedullary (EM) plate fixation because it is biomechanically stronger [5]. In case of stable OTA 31-A1 fractures, either EM or IM implants may be used. In case of unstable OTA 31-A2 and 31-A3 fractures, IM implants are preferably used.

In this regard, a trochanteric fracture is a fracture of the femur being located in the trochanteric region of the femur. To be more precisely, these fractures are denoted as pertrochanteric fractures in case they extend from above outside inwards and downwards (according to the AO classification these fractures are denoted as A1 and A2 fractures). Trochanteric fractures showing the inverse course, i.e., extending from above inside downwards and outwards are frequently termed reversed pertrochanteric or intertrochanteric (e.g. A3 fractures according to the AO classification).

An unsolved problem in the stabilisation of pertrochanteric fractures is the fixation of posterior fracture fragments of the greater trochanter, i.e. fragments that are located on the backside of the femur when looking on the frontside of the patient that often cannot be fixed by the IM nail itself. Due to muscular insertions on such fragments secondary dislocation frequently occurs when such fragments are not properly held in place. As a consequence the muscular shortening may lead to a limping gait because of abductor weakness.

Similar problems occur in case of a trochanteric fracture in combination with partial or total hip arthroplasty. Fracture of the greater trochanter while performing arthroplasty or after surgery because of a simple fall is a well-known complication.

With the existing IM implants there is no possibility to fix above mentioned fragments. If a surgeon decides to fix the fragment by additional means, he usually has to use cerclage cable wires, strong suture fibres or an additional, separately fixed implant. Such existing implants are rather large in size and need large surgical approaches as well.

With the existing EM implants there are additional plates to fix the trochanter on the market. The disadvantage is that the implant is biomechanically weaker and the implant large in size demanding large surgical approaches.

Based on the above, the problem underlying the present invention is to provide an implant device that is capable of stabilizing a region of the greater trochanter, particularly capable of fixing at least one fragment of the greater trochanter originating from an (e.g. pertrochanteric) fracture of the femur in a comparatively simple and effective way, particularly with minimal additional damage of tissue through the surgical approach.

This problem is solved by an implant device having the features of claim 1.

According thereto, the rigid element is designed as a hook-shaped plate being designed to surround the greater trochanter of the femur at least in sections when being arranged in said fastened state and when said femur implant is arranged in (or eventually also on) the femur, particularly in or on the shaft of the femur, as intended. Particularly, said hook-shaped plate (also denoted as trochanteric hook-plate) is particularly designed to encompass the greater trochanter (in said fastened state) such that a fragment of the greater trochanter, particularly a posterior fragment, is properly held in place by means of said hook-shaped plate, particularly so as to prevent said fragment from a dislocation (e.g. in the postero-superior direction) caused by the muscles inserting on the fragment, e.g. abductors and outer rotators, wherein particularly in the present context the gluteus medius is the most relevant one. Thus, the design of the hook-shaped plate directly addresses the tension forces of the muscles, and particularly allows for dimensions of the hook-shaped plate that are by far smaller than the ones of existing implants. As a result, the implant device according to the invention particularly allows for avoiding limping gait fragment dislocation (i.e. muscular shortening).

Figure 5:
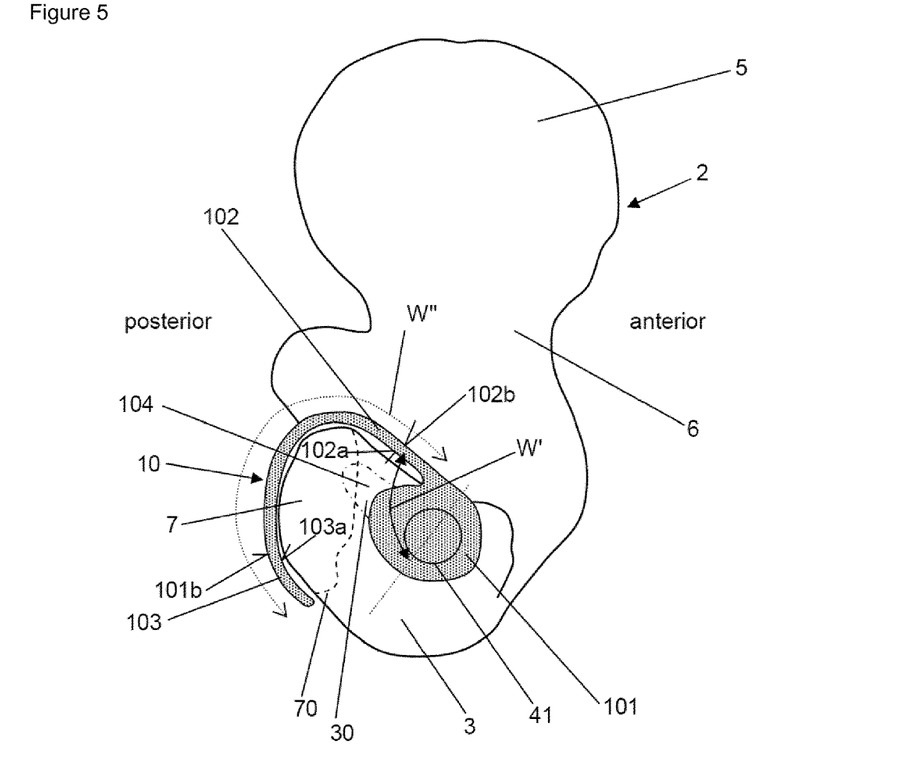
FIG. 5 shows a plan view onto the proximal part of the femur from above with the tip of the greater trochanter, the greater trochanter, the lesser trochanter and the femoral neck and the femoral head.

Particularly, the notion hook-shaped plate does preferably not mean that said plate comprises one or several hooks that are designed to claw/puncture into the femur, but particularly rather the three-dimensional shape/course of the plate itself (cf. FIG. 5 for instance). Thus, particularly, one may refer to the hook-shaped plate also simply as plate.

According to an aspect of the invention, the hook-shaped plate is an add-on device, i.e., is particularly designed to be fastened to an (existing) femur implant. Such femur implants like IM (intramedullary) nails or femoral stems may be designed for insertion into the intramedullary cavity of the femur shaft so that their longitudinal axes along which the respective femur implant extends are oriented along the longitudinal axis of the shaft of the femur.

According to a further aspect of the invention, the hook-shaped plate is designed to be fastened to an (e.g. axial or free) end of said femur implant, which is accessible when the femur implant is arranged in the intramedullary cavity (or—in case of an extramedullary femur implant—even on the femur) as intended. In case of a femur implant in the form of a femoral stem, for instance, the hook-shaped plate may be designed to be fastened to a shoulder of said femur implant.

For fastening the hook-shaped plate to said femur implant, the hook-shaped plate comprises a fastening region according to an aspect of the invention, which preferably extends along a 2D extension plane, i.e. comprises a flat shape.

Said fastening region is preferably integrally connected to a particularly elongated first arm of the hook-shaped plate, which is preferably integrally connected to a particularly elongated second arm of the hook-shaped plate, wherein particularly said second arm is merely connected to the fastening region via the first arm.

According to a further aspect of the present invention, the hook-shaped plate may comprise a third arm integrally connected to the fastening region.

According to a further aspect of the invention, the fastening region and the first arm preferably enclose an angle between 80° and 100°, preferably between 85° and 95°, preferably 90°.

According to a further aspect of the invention, the first arm is tilted with respect to an extension plane along which the fastening region extends, i.e., extends diagonally downwards from the fastening region.

According to a further aspect of the invention, for surrounding the greater trochanter in the fastened state of the hook-shape plate (when the femur implant is arranged in or on the respective femur, particularly in or on the shaft of the femur, as intended), the first arm coming off the fastening region opposes the second arm, wherein the greater trochanter is arranged between said first and said second arm, while the fasting region preferably covers e.g. the tip of the greater trochanter, the fossa piriformis or fossa trochanterica, depending on which of said regions is used as an entry point to the intramedullary cavity. For IM nails, usually the tip of the trochanter is used as said entry point.

According to a further aspect of the invention, the first and the second arm together comprise the course (or shape) of a section of a spiral.

According to a further aspect of the invention, the first and the second arm together encompass the greater trochanter or said region by preferably at least an angle of 150°, preferably at least an angle of 160°, preferably at least an angle of 170°, preferably at least an angle of 180° (when seen from above, i.e., along a direction normal to the extension plane of the fastening region, wherein an angle of 180° corresponds to encompassing at least half the periphery of the greater trochanter) The distance along said direction between the fastening region and a tip (free end) of the second arm may be in the range between 3 cm and 5 cm, particularly between 3.5 cm and 4.5 cm, preferably 4 cm.

According to a further aspect of the invention the first and/or second arm of the hook-shaped plate each comprise an inner side facing the greater trochanter in the fastened state of the hook-shaped plate, wherein the inner side of the first and/or second arm (and eventually also of the third arm) is designed to butt against a surface of the greater trochanter (in said fastened state of the hook-shape plate), e.g. against at least a fragment of the greater trochanter, particularly originating from a pertrochanteric fracture of the femur, such as a posterior fragment of the greater trochanter, so as to fix/support said at least one fragment to the greater trochanter or to stabilize a respective region of the greater trochanter.

According to a further aspect of the invention, in said fastened state of the hook-shaped plate and when the femur implant is arranged in or on the femur, particularly in or on the shaft of the femur, as intended, the first arm extends over the neck of the femur (or a position where the neck would be) between the greater trochanter and the head of the femur (or a position where the head would be).

At the same time, according to a further aspect of the invention, the hook-shaped plate is designed such that its second arm extends along a side of the greater trochanter facing away from the head of the femur (with respect to said fastened state and when the femur implant is arranged in or on the femur, particularly in or on the shaft of the femur, as intended).

Preferably, the hook-shaped plate is formed out of a metal, e.g. steel or Titan, wherein in case the used femur implant (e.g. IM nail) is made out of steel, a hook-shape plate made out of steel is preferably employed, whereas, when the femur implant is made out of Titan, the hook-shaped plate is preferably also made out of Titan.

Particularly, according to a further aspect of the invention, the hook-shaped plate may be formed from a (flat) blank extending along a two-dimensional extension plane by bending (deforming) said blank at least in a transition region integrally connecting a first section of the blank corresponding to the fastening region of the hook-shaped plate to a second section of the blank corresponding to the first arm of the hook-shaped plate as well as by bending said blank in a further transition region integrally connecting said second section of the blank to a third section of the blank corresponding to the second arm of the hook-shaped plate. Preferably, before the blank is bent/deformed, the third section of said two-dimensional blank encloses an obtuse angle with the second section of the two-dimensional blank. Preferably, the hook-shaped plate is delivered comprising its final (bent) hook-shape, although corrections/adjustments can be performed by deforming the final shape accordingly (for customization) when necessary.

In order to fasten the hook-shaped plate to the femur implant, the implant device preferably comprises a fastening means according to a further aspect of the invention, which is particularly designed to fasten the hook-shape plate to said end (or shoulder) of the femur implant, wherein the hook-shaped plate is particularly fastened to the fastening means via the fastening region of the hook-shaped plate in said fastened state of the hook-shaped plate.

Particularly, the fastening region comprises a (through-) opening for fastening the fastening region of the hook-shaped plate to the fastening means, through which opening a screw of said fastening means can be passed so that a head of the screw rests on a boundary region of the fastening region delimiting said opening in particular.

Preferably, said screw is designed to be screwed into an opening provided in the fastening means, which opening particularly comprises a first inner thread that engages with the thread of said screw.

According to a further aspect of the present invention said opening of the fastening means is formed in a separate first element of the fastening means that is designed to be inserted into an opening formed in a face side of the end (or shoulder) of the femur implant, wherein the first element particularly comprises an outer thread that is adapted for being screwed into a corresponding second inner thread formed in the opening of the end of the femur implant.

According to yet a further aspect of the present invention the fastening region comprises an inner side comprising a first notched region, which is designed to engage with a second notched region formed on the fastening means, when the fastening region is pressed, particularly by means of said screw, with its first notched region against the second notched region of the fastening means, so as to fix the fastening region of the hook-shaped plate in a rotationally stable manner on the fastening means with respect to a rotation axis (e.g. longitudinal axis of the femur implant/end region of the femur implant) running perpendicular to the extension plane of the fastening region while allowing also for easily adjusting the angle of the fastening region about said rotation axis before tightening said screw.

Particularly, the second notched region is formed on an upper side of a separate second element of the fastening means, which is preferably adapted to be inserted into the opening of the femur implant.

Preferably, said second element comprises at least one protrusion being designed to engage in a form-fitting manner with a corresponding recess formed in a side wall of the femur implant when the second element is inserted into the opening of the femur implant as intended, which side wall surrounds said opening of the femur implant. Thus, the second element can be prevented from rotating about the longitudinal axis of the femur implant.

In order that the screw for fixing the fastening means can reach the opening of the first element, the second element preferably comprises an opening that is designed to be aligned with the opening of the fastening region as well as with the opening of the first element, when the first and the second element are inserted into the opening of the femur implant as intended (and when the fastening region butts with its first notched region against the second notched region of the second element as intended).

Preferably, said screw is designed to extend through the opening of the fastening region and the opening of the aligned second element when screwed into the aligned opening of the first element such that the screw presses the fastening region against the second element and the second element against the first element and particularly against the at least one recess (side wall).

Preferably, as described above, the implant device is an add-on device that can be used with existing femur implants comprising the above described opening having an inner thread as well as particularly the at least one recess in the side wall surrounding said face side opening of the femur implant, which recess is usually engaged with a corresponding part of a closure cap that is usually used to close said opening of the femur implant.

However, according to a further aspect of the current invention, said femur implant is a component of the implant device according to the invention, wherein particularly the femur implant is formed as an intramedullary nail or femoral stem.

Furthermore, it is an object of the invention to propose a method for implanting an implant device in the form of a hook-shaped plate, particularly according to one of the claims 1 to 15, wherein the method comprises the steps of:
  arranging a femur implant in or on the femur (e.g. of a person), particularly in or on the shaft of the femur, and fastening the hook-shaped plate to said femur implant such that the hook-shaped plate encompasses the greater trochanter of the femur at least in sections.

Particularly, the femur implant is firstly arranged in or on the femur and fixed with respect to the femur (see e.g. above). Thereafter, the hook-shaped plate is fastened to the femur implant. Preferably, the femur implant is an IM nail or a femoral stem. However, the hook-shaped plate may also be fastened to the femur implant before arranging the latter with respect to the femur and may be eventually adjusted with respect to the femur.

Particularly, the hook-shaped plate is fastened to an (e.g. axial or free) end or a shoulder (femoral stem) of the femur implant.

Particularly, the hook-shaped plate comprises a fastening region, wherein the hook-shaped plate is fastened via said fastening region to said femur implant, as well as a first arm integrally formed with the fastening region, and a second arm integrally formed with the first arm, wherein said second arm is merely connected to the fastening region via the first arm, wherein particularly the hook-shaped plate further comprises a third arm integrally connected to the fastening region (see also above).

Particularly, the first arm opposes the second arm, wherein the hook-shaped plate is fastened to the femur implant (or arranged with respect to the femur) such that it encompasses the greater trochanter, particularly a posterior region of the greater trochanter, particularly such that the greater trochanter or said region is arranged between said first and said second arm.

Particularly, the hook-shaped plate is fastened to the femur implant (or arranged with respect to the femur) such that the first and/or the second arm press against at least a fragment of the greater trochanter, particularly originating from a pertrochanteric fracture of the femur, particularly a posterior fragment of the greater trochanter so as to fix said at least one fragment to the greater trochanter.

Particularly, the hook-shaped plate is fastened to the femur implant (or arranged with respect to the femur) such that the first arm extends along the neck of the femur (or a position where the neck would be) between the greater trochanter and the head of the femur (or a position where the head would be).

Particularly, the hook-shaped plate is fastened to the femur implant (or arranged with respect to the femur) such that the second arm extends along a side of the greater trochanter facing away from the head of the femur.

Further features and advantages of the invention shall be described by means of detailed descriptions of embodiments with reference to the Figures, wherein

FIG. 16 shows a perspective view of a femoral stem, to which the hook-shaped plate can also be fastened as an add-on.

Figure 1:
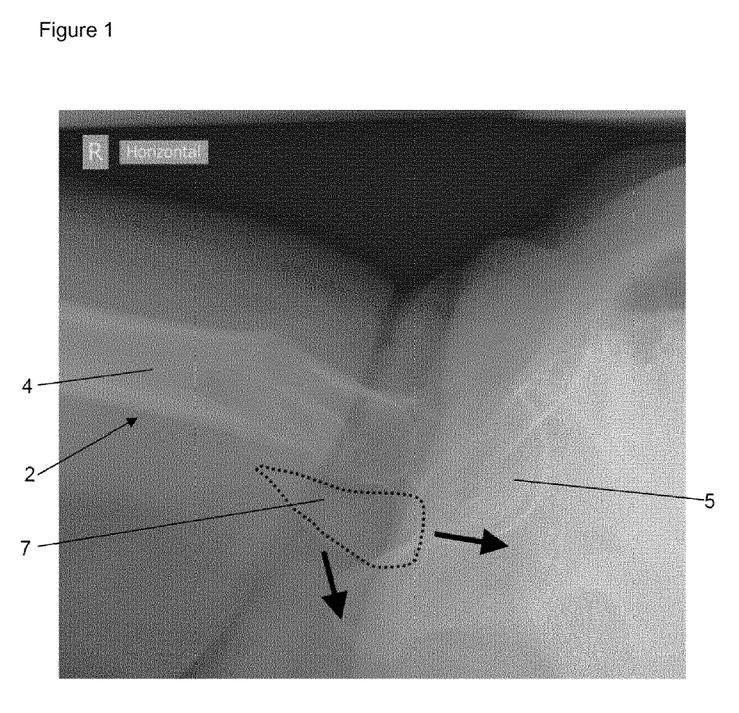
FIG. 1 shows an x-ray image of a pertrochanteric fracture of the femur, wherein a posterior fragment of the greater trochanter is indicated by means of a dotted line as well as dislocation directions due to muscles inserting on said fragment by means of arrows.
Figure 2:
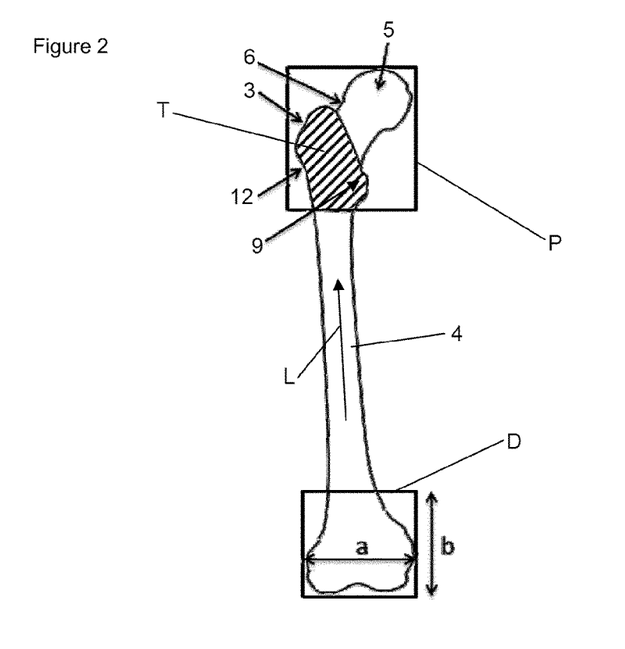
FIG. 2 shows a schematical view of the anterior side of the femur.

FIG. 1 shows a view of a pertrochanteric fracture including a posterior fracture fragment 7 of the greater trochanter 3 of the femur 2, which—as shown schematically in FIG. 2 comprises a femur shaft 4 extending along a longitudinal axis L from the distal femur D being defined as a square (end region) given by the largest diameter in the condylar region (a=b) towards the proximal femur P being (end region) defined as the region of the femur 2 from the top of the femoral head 5 to the lower margin of the lesser trochanter 9. The so-called trochanteric region T is hatched in FIG. 2 and comprises the greater trochanter 3 the innominate tubercle 12 as well as the lesser trochanter 9. The trochanteric region is connected to the head 5 of the femur 2 via the neck 6 of the femur 2.

Figure 3:
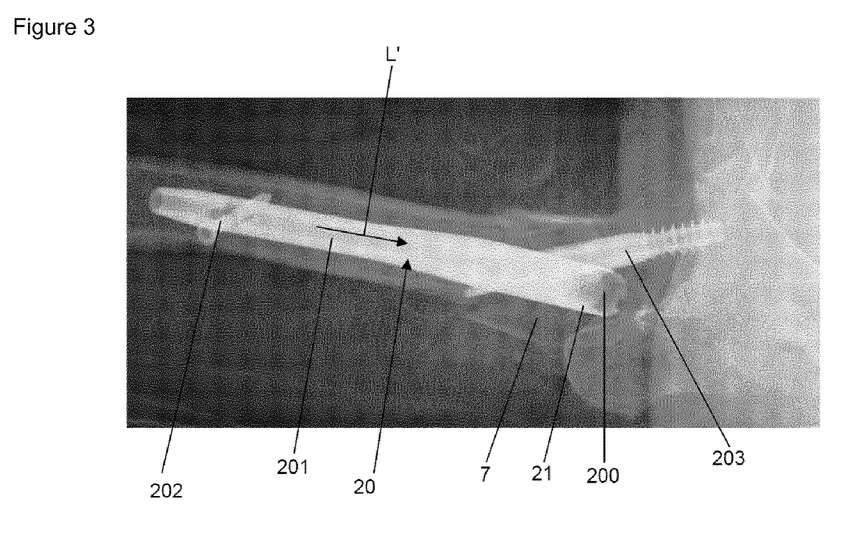
FIG. 3 shows an x-ray image of the fracture according to FIG. 1, which is fixed by means of an IM nail.

FIG. 3 shows a fixation of the pertrochanteric fracture according to FIG. 1 by means of a femur implant 20 in the form of an intramedullary (IM) nail 20 comprising an elongated main body 201 extending along a longitudinal axis L', which aligns with said longitudinal axis L of the shaft 4 of the femur 2, in the intramedullary cavity 11 of the shaft 4 of the femur 2, wherein said shaft 4 is for instance introduced via a tip 30 of the greater trochanter 3 or via another entry point (see above). The IM nail main body 201 may comprise a curvature at its (axial or free) end 21 proximal to the greater trochanter 3, when the entry point is not aligned with the longitudinal axis L of the femoral shaft 4. The femur implant 20 further comprises at least one locking screw 202 arranged at a further (axial or free) end of the main body 201 of the femur implant 20, which further end is distal to the head 5/greater trochanter 3 of the femur 2, wherein said locking screw 202 extends across or under an angle with respect to the longitudinal axis L' of the main body 201 through the latter and secures the main body 201 with respect to the femur shaft 4. The femur implant 20 comprises a further screw 203 in the region of the end 21 of the femur implant 20/main body 201, which further screw 203 extends through the main body 203 as well as through the neck 6 of the femur 2 into the head 5 of the femur 2 in order to fix said fracture.

Figure 4:
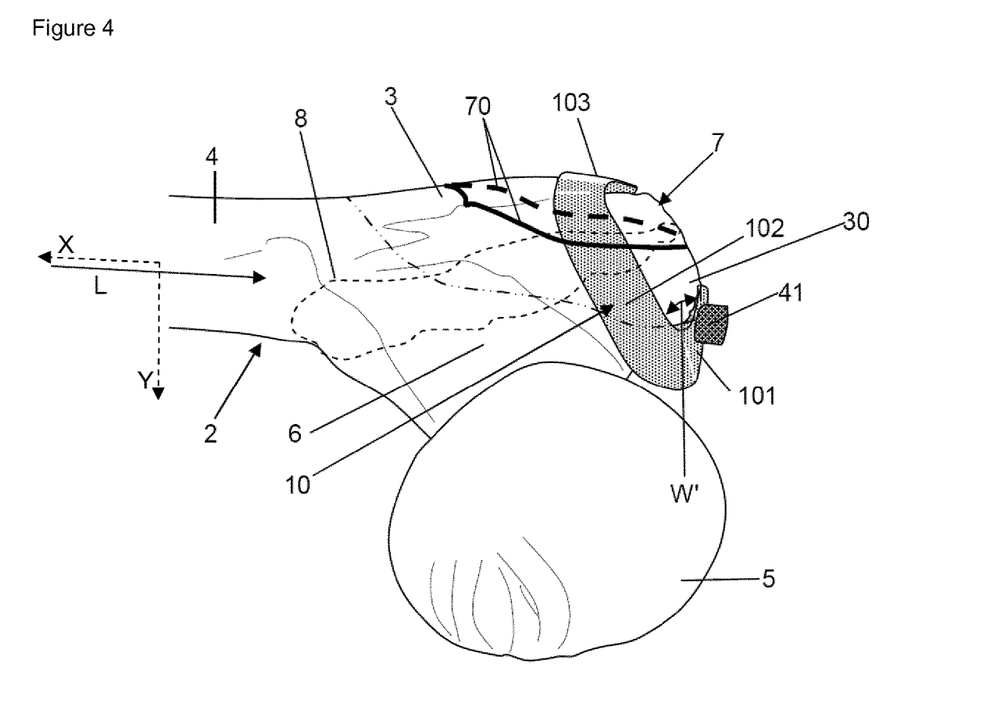
FIG. 4 shows the posterior aspect of the femur as well as the implant device according to the invention, which is used to hold the (posterior) fragment according to FIGS. 1 and 3 in place so as to prevent a dislocation of the fragment due to a muscle inserting on said fragment.

The implant device 1 according to the invention as shown for instance in FIGS. 4 and 5 now also allows for fixing fragments 7 (indicated by the bold solid and dashed lines 70 in FIG. 4) originating from said fracture of the femur 2 as described above (an exemplary fracture line/contour 8 is indicated in FIG. 4). Such a fragment 7 in the form of a posterior fragment 7 may tend to dislocate along the black arrows indicated in FIG. 1, i.e. in a postero-superior dislocation direction, due to muscles inserting on said fragment 7. This may be prevented by the implant device 1 according to the invention as described in the following.

As shown in FIGS. 4 and 5 in conjunction with FIGS. 6 to 16, the implant device 1 comprises a hook-shaped plate 10 being designed to surround the greater trochanter 3 as well as said fragment 7 in a fastened state, in which said implant device 1 is fastened to an existing femur implant 20 (here in the form of an IM nail 20 as described above), which is implanted into the intramedullary cavity 11 of the shaft 4 of the femur 2.

Figure 6:
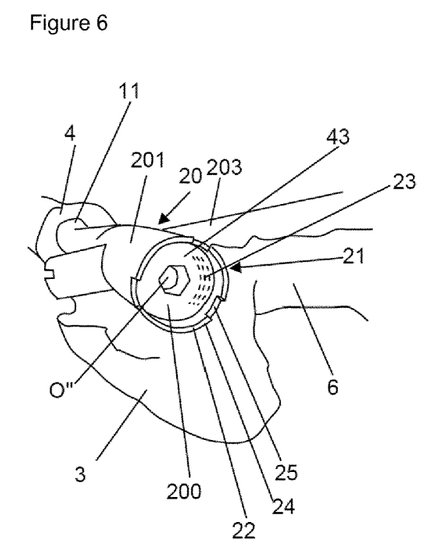
FIG. 6 shows a perspective view of an IM nail implanted into the intramedullary cavity of a femur, wherein a part of the femur is removed in order to show the IM nail and the opening at the end of the IM nail, in which opening a first element of a fastening means is inserted that is used for fastening the implant device according to the invention to the IM nail.
Figure 7:
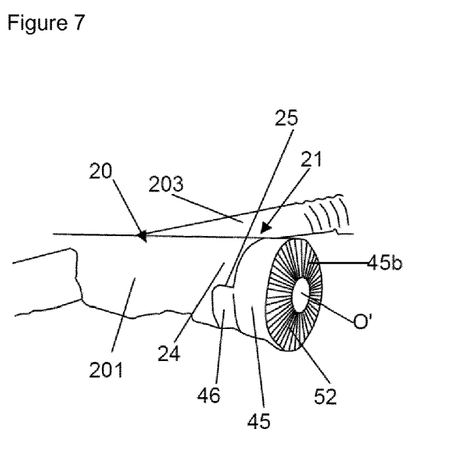
FIG. 7 shows another perspective view of the IM nail according to FIG. 6, wherein also a second element of the fastening means is inserted into said opening of the IM nail, which second element closes said opening of the IM nail and serves for fixing the hook-shaped plate to the fastening means and thus to the IM nail.
Figure 8:
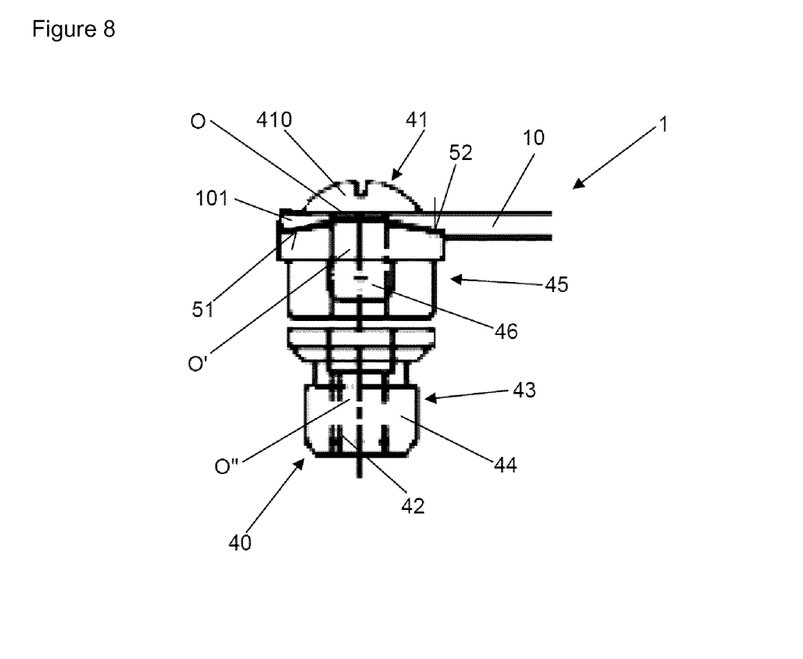
FIG. 8 shows a cross-sectional view of the implant device according to the invention, namely the fastening means comprising the first and the second element as well as the hook-shaped plate being fastened to the first and second element by means of a screw connecting the latter elements.
Figure 9:
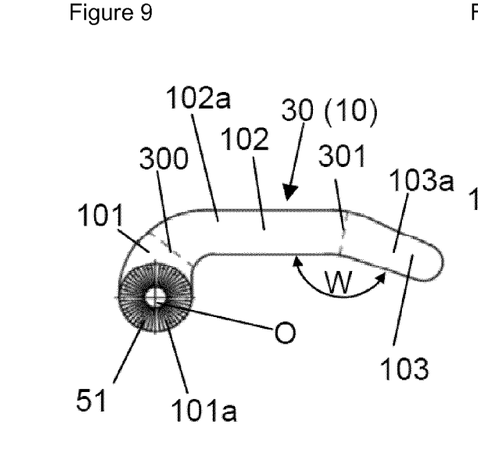
FIG. 9 shows a plan view of a lower (inner) side of a blank for forming the hook-shaped plate.
Figure 10:
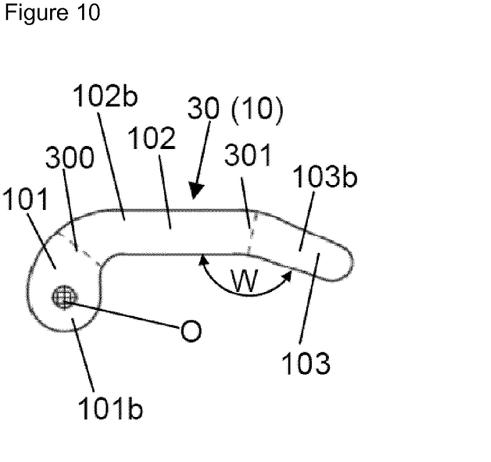
FIG. 10 shows a plan view of an upper (outer) side of the blank according to FIG. 9.
Figure 11:
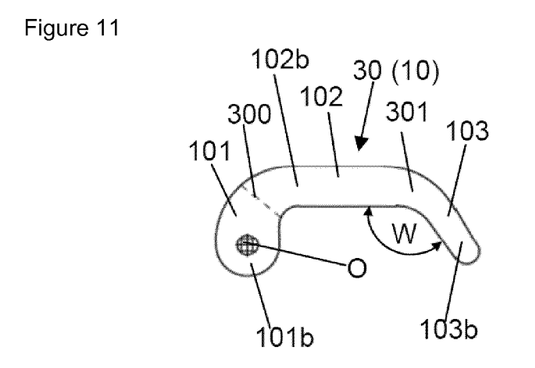
FIGS. 11-15 show plan views of a variety of upper (outer) sides of different blanks for forming the respective hook-shaped plate.
Figure 12:
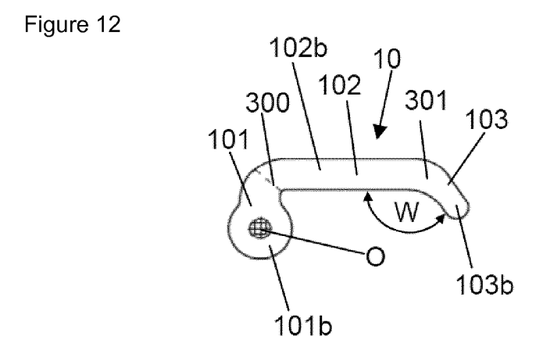
Figure 13:
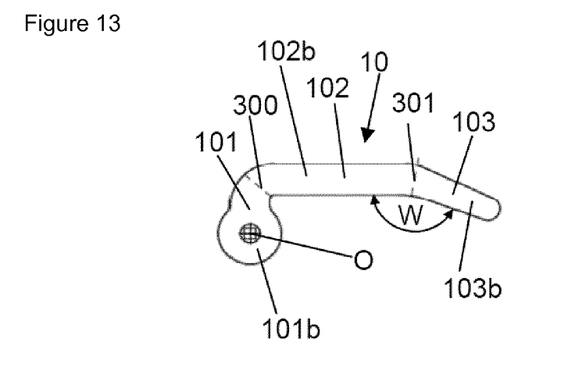

For this, the hook-shaped plate 10 comprises a fastening region 101 via which the plate 10 is fastened to a fastening means 40, via which in turn the plate 10 is fastened to the existing femur implant 20 (cf. FIGS. 6 to 8).

The fastening region 101 comprises an inner side 101a (contributing to an inner side of the plate 10 that faces/contacts the femur 2) as well as an outer side 101b facing away from said inner side 101a of the fastening region 101 and the femur 2 (which outer side 101b of the fastening region 101 contributes to the outer side of the plate 10 facing away from the femur 2).

The fastening region 101 of the plate 10 is integrally formed with a first arm 102 of the plate 10, which extends from the fastening region 101, which covers a part of the tip 30 of the greater trochanter 3 (entry point of the femur implant 20), along a side of the greater trochanter 3 facing the femoral head 5 as shown in FIGS. 4 and 5 with an outer surface 102b of the first arm 102 while facing (the inner aspect of) the greater trochanter 3 with an inner surface 102a (facing away from said outer surface 102b) of the first arm 102.

The fastening region 101 and the first arm 102 may butt against the fastening means 40 and an underlying portion of the femur 2 (greater trochanter 3/fragment 7) via their inner sides 101a, 102a, respectively.

Further, the first arm 102 is integrally formed with a second arm 103 of the plate 10, wherein the second arm 103 also comprises an inner side 103a for butting against an underlying region of the femur 2 (greater trochanter 3/fragment 7) as well as an outer side 103b facing away from the inner side 103a of the second arm 103. In FIG. 4 the inner sides 101a, 102a, and 103a are not visible, but are shown in FIG. 5 and FIGS. 9 to 15 showing the plate 10 spread along a two-dimensional extension plane (paper plane).

The two arms 102, 103 of the plate 10 form—when looking on the outsides 102b, 103b of the two arms 102, 103—a convex (spiral-like) configuration (curvature) so as to be able to encompass the greater trochanter 3, namely a posterior fragment 7 of the latter, wherein said inner sides 102a and/or 103a of the two arms 102, 103 preferably butt against the greater trochanter 3 particularly against said posterior fragment 7.

Due to this course of the hook-shaped plate 10, a typical (posterior) fragment 7 of the greater trochanter 3 is held in place by means of the first and/or the second arm 102, 103 so that it cannot be dislocated, e.g. by muscles inserting on it.

As shown in FIGS. 9 to 15 the hook-shaped plate 10 can be formed from two-dimensional blanks 30, i.e., thin flat blanks 30 (e.g. out of a steel or Titan) that can be bent into the respective shape of the respective plate 10 by bending them at least in two transition regions 300, 301.

Also in case the plate 10 is manufactured differently, FIGS. 9 to 15 show the geometry of the hook-shaped plate 10 when the letter is fictitiously spread along a two dimensional extension plane (paper plane).

Then, as can be seen in FIGS. 9 to 15, the blank 30/plate 10 comprises a first section 101 (corresponding to the fastening region) being integrally connected to a second section 102 of the blank 30 (corresponding to the first arm) extending (essentially) linearly towards a third section 103 (corresponding to the second arm), which in turn is integrally connected with the second section 102 and extends linearly—albeit in a different direction—such that the second and the third section 102, 103 enclose an obtuse angle W in said two-dimensional state of the blank 30. The first section 101 and the second section 102 are integrally connected via a transition region 300 (for instance a line or an area), wherein the second section 102 and the third section 103 are integrally connected via a further transition region 301 (for instance an line or an area), wherein the 3D shape of the plate 10 can essentially be generated by bending said blanks at least in said transition regions 300, 301 and eventually also in other areas.

When the hook-shaped plate 10 comprises its actual shape for encompassing the greater trochanter 3/posterior fragment 7, the course of the hook-shape plate 10 can be inferred from FIGS. 4 and 5. According thereto (when seen from above along a direction normal to the fastening region 101), the fastening region 101 and the first arm 102 enclose an angle W' of approximately 90°, wherein the first arm 102 is tilted with respect to the extension plane along which the fastening region 101 extends such that the first arm 102 runs downwards in an inclined manner. Finally, the first and the second arm 101, 102 preferably enclose an angle W'" of at least 180° (e.g. approximately half the periphery of the greater trochanter 3) as indicated by the dotted line in FIG. 5, wherein they comprise (essentially) a course/shape of a section of a spiral (corkscrew). Particularly, when including also the fastening region 101, the plate 10 encloses an angle of at least 270° (seen from above along said normal).

In order to fasten the hook-shaped plate 10 to the femur implant 20 (i.e. to its main body 201), the femur implant 20 (main body 201) comprises at its end 21 (proximal to the greater trochanter 3) a face side 22, in which an opening 200 of the femur implant 20 is formed that is delimited by a surrounding side wall 24 comprising preferably three recesses 25 in the form of cut-outs formed in the side wall (face side) 24. The opening 200 comprises an inner thread 23 denoted here as second inner thread 23.

Now, said fastening means 40 preferably comprises a first element 43 having a lateral surface with an outer thread 44 that is adapted to said second inner thread 23 of the opening 200 of the femur implant 20, so that said first element 43 can be screwed into the opening 200 of the femur implant 20 engaging with the second inner thread 23.

Further, the fastening means 40 comprises a separate second element 45 on top of the first element 43, which aligns with the first element 43 when both elements 43, 45 are properly inserted into the opening 200 of the femur implant 20, and comprises protrusions 46 protruding from a lateral surface of the second element 45, which engage in a form-fitting manner with the recesses 25 of the side walls 24 when the second element 45 is inserted into the opening 200 of the femur implant 20 so that the second element 45 cannot be rotated about said rotation axis (e.g. the longitudinal axis L' of the femur implant 20 (main body 201)) when being inserted into said opening 200 as intended.

For fixing the fastening region 101 of the plate 10 to the fastening means 40, which itself is fastened to the femur implant 20 via the outer thread 44 of the first element 43 and the second inner thread 23 of the femur implant's face sided opening 200, the fastening region 101 comprises a central opening O through which a screw 41 of the fastening means 40 is passed so that a head 410 of the screw 41 rests on a boundary region of the outer side 101b of the fastening region 101 delimiting said opening O of the fastening region 101, wherein the screw 41 extends through an opening O' of the second element 45 that is aligned with the opening O of the fastening region 101 as well as into an opening O" of the first element 43, which comprises a first inner thread 42 that is adapted for being screwed with the thread provided on said screw 41. Thus, the screw 41—when tightened—presses the fastening region 101 with its inner side 101a against an upper side 45b of the second element 45, which in turn is pressed with its projections 46 into the recesses 25 and against the first element 43.

In order to adjust the fastening region 101 on the upper side 45b of the second element 45 concerning an angle about said rotation axis (e.g. the longitudinal axis L' of the femur implant 20 (main body 201)), both the inner side 101a of the fastening region 101 as well as the upper 45b side of the second element 45 facing the inner side 101a of the fastening region 101 comprise a notched region 51, 52, such that—when said screw 41 is tightened—the first notched region 51 of the fastening region 101 engages with the second notched region 52 of the second element 45, which drastically increases the friction between the fastening region 101 and the second element 45 and thus prevents the plate 10 from rotating about said rotation axis. Preferably, in the implanted state, particularly merely the upper side 45b of the second element 45 projects out of the femur, so that the plate 10 can be fixed to the second element 45 without interference of parts of the femur 2.

Figure 14:
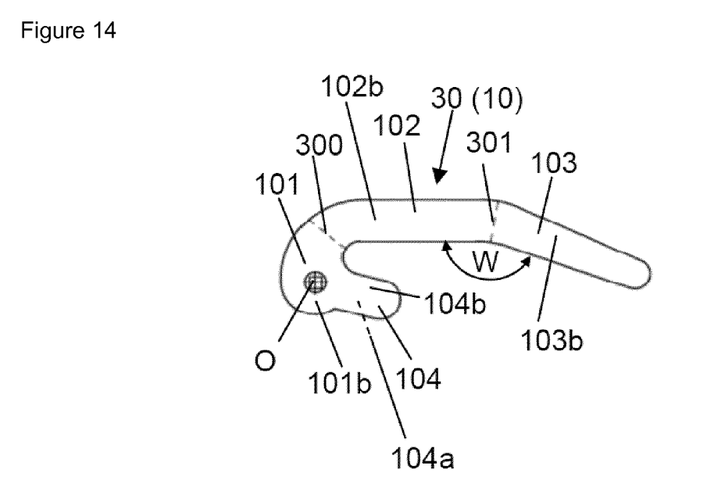
Figure 15:
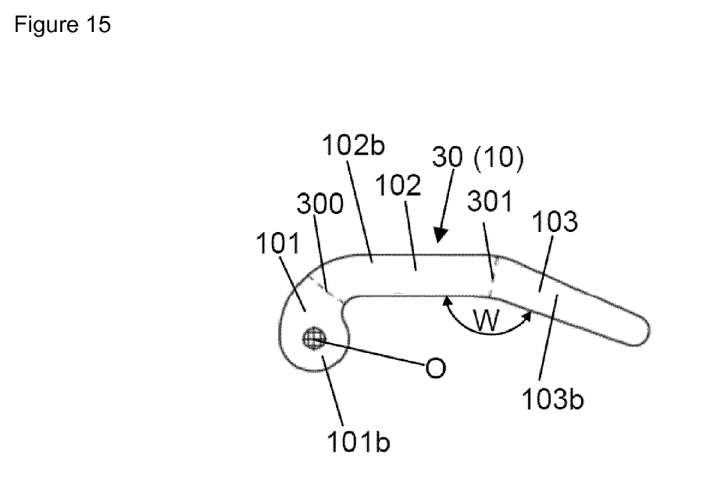

As can be seen from FIGS. 5 and 14, the plate 10 may also comprise a third arm 104 (fourth section) having an inner side 104a facing the tip 30 of the greater trochanter 3 in a posterior direction as well as an outer side 104b facing away from said inner side 104a, which third arm 104 may be integrally connected to the fastening region 101 (first section), wherein the third arm 104 may essentially extend along the first arm 101 with respect to the two-dimensional representation of the plate according to FIG. 14.

Figure 16:
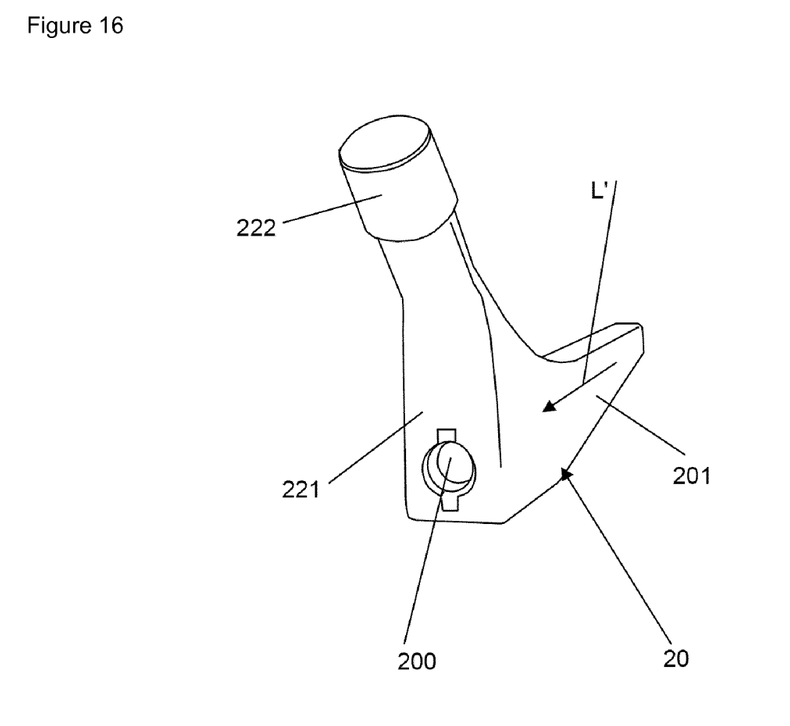

Further, FIG. 16 shows a femoral stem 20, which can be inserted into the intramedullary cavity 11 of the femur 2 with its main body 201 extending along a longitudinal axis L'. The femoral stem 20 comprises an end 222 that extends from a shoulder 221 of the femoral stem 20, to which end 222 a spherical head can be fastened that forms a substitute for the head 5 of the femur 2. Further, the femoral stem 20 comprises an opening 200 arranged on the shoulder 221 by means of which the hook-shaped plate 10 described herein can be fixed with help of a fastening means to the femoral stem 20. The fastening means may comprise or may consist of a screw that can be screwed into said opening 200, which comprises an inner thread corresponding to the outer thread of said screw.

Finally, the behavior of the implant 10 according to the invention when used with an IM nail as shown in FIGS. 5 to 7 was also tested under dynamic loading and compared to a known trochanteric fixation plate with respect to a femur model, wherein the relative movement of the greater trochanter fragment (e.g. fragment 7 of FIG. 4) with respect to the femur (model) 2 was recorded. According thereto, the magnitude of the fragment displacements along the femoral axis X indicated in dashed lines in FIG. 4 was smaller for the implant device 10 according to the invention than for the traditional trochanteric fixation plate system. Such a smaller movement of the fragment along said axis X is preferred, since one wants the fragment to move as little as possible with respect to the femur. The movement in medio-lateral direction (i.e. along axis Y indicated in dashed lines in FIG. 4) was similar for both systems.

REFERENCES

[1] Kannus P, Parkkari J, Niemi S, et al. Prevention of hip fracture in elderly people with use of a hip protector. N Engl J Med 2000; 343:1506-13.

[2] Kannus P, Niemi S, Parkkari J, et al. Hip fractures in Finland between 1970 and 1997 and predictions for the future. Lancet 1999; 353:802-5.
[3] Gjertsen J E, Engesaeter L B, Fumes O, et al. The Norwegian hip fracture Register: Experiences after the first 2 years and 15,576 reported operations. Acta Orthop 2008; 79(5):583-93.
[4] Lohmann R, Frerichmann U, Stöckle U, et al. Proximal femoral fractures in the elderly. Analysis of data from health insurance providers on more than 23 millions injured persons—part 1. Unfallchirurg. 2007; 110(7):603-9.
[5] Parker M J, Handoll H H, Bhonsle S, et al. Condylocephalic nails versus extramedullary implants for extracapsular hip fractures. Cochrane Database Syst Rev. 2000; (2); CD 000338

The invention claimed is:

1. An implant device, comprising:
a rigid element (10) being designed to be fastened to a femur implant (20) in a fastened state of said rigid element (10), wherein
said rigid element (10) is designed as a hook-shaped plate for encompassing at least a section of the greater trochanter (3) of a femur (2) when being arranged in said fastened state and when said femur implant (20) is implanted in the femur (2), and wherein
the rigid element (10) comprises a fastening region (101), wherein the rigid element (10) is configured to be fastened via said fastening region (101) to said femur implant (20), as well as a first arm (102) integrally formed with the fastening region (101), and a second arm (103) integrally formed with the first arm (102), wherein said second arm is (103) connected to the fastening region (101) via the first arm (102), and wherein
in said fastened state and when the femur implant (20) is implanted in the femur, the first arm (102) extends along the neck (6) of the femur (2) between the greater trochanter (3) and the head (5) of the femur (2), and wherein
in said fastened state and when the femur implant (20) is implanted in the femur, the second arm (103) extends along a side of the greater trochanter (3), which side of the greater trochanter (3)-faces away from the head (5) of the femur (2), and wherein
the implant device (1) comprises a fastening means (40) for fastening the rigid element (10) to the femur implant (20), wherein the fastening region (101) comprises an opening (O) for fastening the fastening region (101) of the rigid element (10) to the fastening means (40), wherein the fastening means (40) comprises a screw (41) being designed to be passed through said opening (O) of the fastening region (101), wherein said screw (41) is designed to be screwed into an opening (O") of the fastening means (40) comprising a first inner thread (42).

2. The implant device according to claim 1, wherein said rigid element (10) is designed to be fastened to an end (21) or a shoulder (221) of said femur implant (20).

3. The implant device according to claim 1, wherein the fastening region (101) and the first arm (102) extend at an angle (W') to each other, wherein the angle is between 80° and 100°.

4. The implant device according to claim 1, wherein the first arm (102) opposes the second arm (103), wherein the rigid element (10) is designed to encompass the greater trochanter (3) in said fastened state and when said femur implant (20) is implanted in the femur (2) such that the greater trochanter (3) is arranged between said first and said second arm (102, 103), wherein the first and the second arm (102, 103) together form a convex curved section of the rigid element (10).

5. The implant device according to claim 1, wherein in said fastened state and when the femur implant (20) is implanted in the femur, the rigid element (10) is designed to press against at least a fragment (7) of the greater trochanter (3) so as to fix said at least one fragment (7) to the greater trochanter (3).

6. The implant device according to claim 1, wherein the rigid element (10) is a bent blank (30) extending along a two-dimensional extension plane, which blank (30) comprises a bending in a transition region (300) integrally connecting a first section (101) of the blank (30) corresponding to the fastening region (101) to a second section (102) of the blank (30) corresponding to the first arm (102) as well as in a further transition region (300) integrally connecting said second section (102) to a third section (103) corresponding to the second arm (103), wherein the third section (103) of said two-dimensional blank (30) encloses an obtuse angle (W) with the second section (102) of the two-dimensional blank (30).

7. The implant device according to claim 1, wherein said opening (O") of the fastening means (40) is formed in a first element (43) of the fastening means (40) that is designed to be fastened to an end (21) of the femur implant (20) in order to fasten the fastening means (40) to the femur implant (20), wherein said first element (43) is designed to be inserted in an opening (200) provided in a face side (22) of the end (21) of the femur implant (20), wherein said first element (43) comprises an outer thread (44), wherein the first element (43) is designed to be screwed with said outer thread (44) into a corresponding second inner thread (23) formed in said opening (200) of the femur implant (20).

8. The implant device according to claim 7, wherein the fastening region (101) comprises an inner side (101a) comprising a first notched region (51), which is designed to engage with a second notched region (52) formed on the fastening means (40), when the fastening region (101) is pressed, by means of said screw (41), with its first notched region (51) against the second notched region (52) of the fastening means (40).

9. The implant device according to claim 8, wherein the second notched region (52) is formed on an upper side (45b) of a second element (45) of the fastening means (40), wherein the second element (45) is designed to be inserted into said opening (200) of the femur implant (20), wherein the second element (45) comprises at least one protrusion (46) being designed to engage in a form-fitting manner with a corresponding recess (25) formed in a side wall (24) of the femur implant (20) when the second element (45) is inserted into the opening (200) of the femur implant (20), which side wall (24) surrounds said opening (200) of the femur implant (20), wherein the second element (45) comprises an opening (O') that is designed to be aligned with the opening (O) of the fastening region (101) and the opening (O") of the first element (43), when the first element (43) and the second element (45) are inserted into the opening (200) of the femur implant (20).

10. The implant device according to claim 9, wherein when the first and the second element (43, 45) are inserted into the opening (200) of the femur implant (20), said screw (41) is designed to extend through the opening (O) of the fastening region (101) and through the opening (O') of the second element (45) when screwed into the opening (O") of the first element (43) such that the screw (41) presses the fastening region (101) against the second element (45), and the second element (45) against the first element (43).

11. An implant device comprising:
a femur implant (20) formed as an intramedullary nail or a femoral stem; and
a rigid element (10) configured to be fastened to the femur implant (20) when the implant device is in a fastened state,
wherein said rigid element (10) is configured as a hook-shaped plate comprised of a fastening region (101) and at least two arms (102, 103), said region and arms form sections of the rigid element operative for attaching to or encompassing the greater trochanter (3) of a femur (2) when said fastening region is fastened to said femur implant when said femur implant (20) is implanted in the femur (2), and wherein
the implant device (1) comprises a fastening means (40) for fastening the rigid element (10) to the femur implant (20), wherein the fastening region (101) comprises an opening (O) for fastening the fastening region (101) of the rigid element (10) to the fastening means (40), wherein the fastening means (40) comprises a screw (41) being designed to be passed through said opening (O) of the fastening region (101), wherein said screw (41) is designed to be screwed into an opening (O") of the fastening means (40) comprising a first inner thread (42).

12. The implant device according to claim 3, wherein the first arm (102) is tilted with respect to an extension plane along which the fastening region (101) extends.

13. The implant device according to claim 4, wherein the first and the second arm (102, 103) together follow a shape of a section of a spiral.

14. The implant device according to claim 4, wherein the first and the second arm (102, 103) together encompass the greater trochanter (3) by at least an angle (W") of 180°.

15. The implant device according to claim 1, wherein the femur implant (20) is formed as an intramedullary nail or a femoral stem.

16. The implant device according to claim 1, wherein the fastening means (40) is configured for fastening the rigid element (10) to an end (21) or a shoulder (221) of the femur implant (20), wherein the rigid element (10) is designed to be fastened to the fastening means (40) through the fastening region (101) in said fastened state.

17. An implant device, comprising:
a rigid element (10) being designed to be fastened to a femur implant (20) in a fastened state of said rigid element (10), wherein
said rigid element (10) is designed as a hook-shaped plate for encompassing at least a section of the greater trochanter (3) of a femur (2) when being arranged in said fastened state and when said femur implant (20) is implanted in the femur (2), and wherein
the rigid element (10) comprises a fastening region (101), wherein the rigid element (10) is designed to be fastened via said fastening region (101) to said femur implant (20), as well as a first arm (102) integrally formed with the fastening region (101), and a second arm (103) integrally formed with the first arm (102), wherein said second arm is (103) connected to the fastening region (101) via the first arm (102), and wherein
the first arm (102) opposes the second arm (103), wherein the rigid element (10) is designed to encompass the greater trochanter (3) in said fastened state and when said femur implant (20) is implanted in the femur (2) such that the greater trochanter (3) is arranged between said first and said second arm (102, 103), wherein the first and the second arm (102, 103) together form a convex curved section of the rigid element (10), and wherein the first and the second arm (102, 103) together follow a shape of a section of a spiral, and wherein the first and the second arm (102, 103) together encompass the greater trochanter (3) by at least an angle (W") of 180°.

18. An implant device, comprising:
a rigid element (10) being designed to be fastened to a femur implant (20) in a fastened state of said rigid element (10), wherein
said rigid element (10) is designed as a hook-shaped plate for encompassing at least a section of the greater trochanter (3) of the femur (2) when being arranged in said fastened state and when said femur implant (20) is implanted in the femur (2), and wherein
the rigid element (10) comprises a fastening region (101), wherein the rigid element (10) is designed to be fastened via said fastening region (101) to said femur implant (20), as well as a first arm (102) integrally formed with the fastening region (101), and a second arm (103) integrally formed with the first arm (102), wherein said second arm is (103) connected to the fastening region (101) via the first arm (102), and wherein
in said fastened state and when the femur implant (20) is implanted in the femur, the first arm (102) extends along the neck (6) of the femur (2) between the greater trochanter (3) and the head (5) of the femur (2), and wherein
in said fastened state and when the femur implant (20) is implanted in the femur, the second arm (103) extends along a side of the greater trochanter (3), which side of the greater trochanter (3) faces away from the head (5) of the femur (2), and wherein
the first arm (102) opposes the second arm (103), wherein the rigid element (10) is designed to encompass the greater trochanter (3) in said fastened state and when said femur implant (20) is implanted in the femur (2) such that the greater trochanter (3) is arranged between said first and said second arm (102, 103), wherein the first and the second arm (102, 103) together form a convex curved section of the rigid element (10), and wherein the first and the second arm (102, 103) together follow a shape of a section of a spiral.

19. An implant device, comprising:
a rigid element (10) being designed to be fastened to a femur implant (20) in a fastened state of said rigid element (10), wherein
said rigid element (10) is designed as a hook-shaped plate for encompassing at least a section of the greater trochanter (3) of the femur (2) when being arranged in said fastened state and when said femur implant (20) is implanted in the femur (2), and wherein
the rigid element (10) comprises a fastening region (101), wherein the rigid element (10) is designed to be fastened via said fastening region (101) to said femur implant (20), as well as a first arm (102) integrally formed with the fastening region (101), and a second arm (103) integrally formed with the first arm (102), wherein said second arm is (103) connected to the fastening region (101) via the first arm (102), and wherein in said fastened state and when the femur implant (20) is implanted in the femur, the first arm (102) extends along the neck (6) of the femur (2) between the greater trochanter (3) and the head (5) of the femur (2), and wherein in said fastened state and when the femur implant (20) is implanted in the femur, the second arm (103) extends along a side of the greater trochanter (3), which side of the greater trochanter (3) faces away from the head (5) of the femur (2), and wherein the first arm (102) is tilted with respect to an extension plane along which the fastening region (101) extends.

* * * * *